United States Patent
Yin et al.

(10) Patent No.: US 9,944,755 B2
(45) Date of Patent: Apr. 17, 2018

(54) OXAZOLINE POLYMER COMPOSITIONS AND USE THEREOF

(71) Applicant: ANP Technologies Inc., Newark, DE (US)

(72) Inventors: Ray Yin, Newark, DE (US); Jing Pan, Newark, DE (US); Dujie Qin, Wilmington, DE (US); Yubei Zhang, Hockessin, DE (US)

(73) Assignee: ANP Technologies, Inc., Newark, DE (US)

( * ) Notice: Subject to any disclaimer, the term of this patent is extended or adjusted under 35 U.S.C. 154(b) by 0 days.

(21) Appl. No.: 15/352,521

(22) Filed: Nov. 15, 2016

(65) Prior Publication Data

US 2017/0066879 A1     Mar. 9, 2017

Related U.S. Application Data

(63) Continuation of application No. 14/236,758, filed as application No. PCT/US2014/049410 on Aug. 3, 2012.

(60) Provisional application No. 61/514,880, filed on Aug. 3, 2011.

(51) Int. Cl.
| | | |
|---|---|---|
| *A61K 8/72* | (2006.01) | |
| *C08G 69/48* | (2006.01) | |
| *C08G 73/02* | (2006.01) | |
| *A61K 47/59* | (2017.01) | |
| *A61K 47/68* | (2017.01) | |
| *A61K 47/50* | (2017.01) | |
| *A61K 47/51* | (2017.01) | |
| *A61K 47/56* | (2017.01) | |
| *A61K 47/54* | (2017.01) | |
| *A61K 47/55* | (2017.01) | |

(52) U.S. Cl.
CPC ............ *C08G 69/48* (2013.01); *A61K 47/595* (2017.08); *A61K 47/6807* (2017.08); *C08G 73/028* (2013.01); *C08G 73/0233* (2013.01); *A61K 47/50* (2017.08); *A61K 47/51* (2017.08); *A61K 47/54* (2017.08); *A61K 47/55* (2017.08); *A61K 47/56* (2017.08)

(58) Field of Classification Search
None
See application file for complete search history.

(56) References Cited

U.S. PATENT DOCUMENTS

| | | |
|---|---|---|
| 2003/0144373 A1 | 7/2003 | Bowman et al. |
| 2006/0041058 A1 | 2/2006 | Yin et al. |
| 2006/0051315 A1 | 3/2006 | Scaria et al. |
| 2008/0311145 A1 | 12/2008 | Campion et al. |
| 2011/0123453 A1 | 5/2011 | Bentley et al. |

OTHER PUBLICATIONS

Yoshiki et al. "Synthesis and Redox Gelation of Disulfide-Modified Polyoxazoline", 1993, Macromolecules, vol. 26, No. 5, pp. 883-887.*

* cited by examiner

*Primary Examiner* — James W Rogers
(74) *Attorney, Agent, or Firm* — Gann G. Xu; MDIP LLC

(57) ABSTRACT

Compositions comprising an oxazoline polymer and optional linkers to carry a variety of molecules.

17 Claims, 10 Drawing Sheets

EOx: Ethyloxazoline

PEOx: Polyethyloxazoline

OXAZOLINE POLYMER COMPOSITIONS AND USE THEREOF

FIELD

The present invention concerns the use of an end-functionalized polyoxazoline polymer comprising, for example, a poly (unsubstituted oxazoline), a poly (substituted oxazoline) polymer or a combination thereof, wherein said polymer can be a linear, branched, randomly branched or dendritically branched polymer. The reactive chain ends of the polyoxazoline polymer, for example, poly (2-methyloxazoline) (PMOX), poly (2-ethyoxazoline) (PEOX), poly (2-propyloxazoline) (PPOX) and poly (2-butyloxazoline) (PBOX), can comprise a small molecule comprising multifunctional, unprotected amino groups or imino groups. Such an end-functionalized polymer then can be linked to or associated with a bioactive material through an additional linker molecule either directly or indirectly, or by physically mixing the polymer and bioactive material bringing the two into association. Alternatively, the initiator portion of said polymer also can be linked with said bioactive material. The resulting composition can be employed in agriculture, environmental studies, diagnostics, drug monitoring, drug target screening, drug lead optimization and therapeutics, for example.

BACKGROUND

Polyoxazoline Polymers

Polyoxazoline (POX) polymers have been used in cosmetic and food packaging applications. Due to good water solubility, POX also has been considered a candidate to replace polyethyleneglycol (PEG) for different biomedical-related applications (Adams, Advanced Drug Delivery Reviews 59 (2007) 1504-1520 and Mero, Journal of Controlled Release 125 (2008) 87-95).

POX polymers comprising, for example, poly (unsubstituted oxazoline) or poly (substituted oxazoline), can be produced by cationic ring opening polymerization. Commonly used water-soluble polymers are PMOX and PEOX. Under living polymerization conditions (e.g., conditions including fast initiation, slow propagation and the lack of chain termination and transfer reactions), a well defined, linear PMOX and PEOX can be produced (Tomalia et al., Macromol. 1991, 24, 1435. Kobayashi, J. Polym. Sci. Part A: Polym. Chem.: Vol. 40 (2002)); while under other synthesis conditions, branched or randomly branched PMOX and PEOX polymers can be generated (Litt, Macromol. Sci. Chem. A9(5), 703-727 (1975) and Yin, U.S. Pat. No. 7,754,500).

Under both types of reaction conditions, an electrophilic (e.g., cationic) chain end can be generated and further reacted with a nucleophilic group or a molecule containing a nucleophilic group so that the polymerization reaction can be terminated. Most known methods for terminating such a reactive chain end use a monofunctional nucleophilic group, such as those consisting of a single imino (—NH—) group, for example, a morpholine or a protected piperazine (Tomalia, U.S. Pat. No. 5,773,527 and Zhang et. al., Macromol., 2009, 42 (6) 2215-2221). That is true for the termination of linear POX polymers, such as a living linear PMOX or PEOX, where a defined chain end can be generated.

The termination of a reactive POX polymer with a polyfunctional polymer to generate star, comb, Starburst or Combburst polymers is described, for example, in Tomalia, U.S. Pat. No. 5,773,527.

However, use of a multifunctional small molecule without any protecting groups to terminate a reactive POX to generate a functional polymer with only one polymer per terminating molecule is not a preferable or a desired way to make a functionalized POX. That approach tends to produce more dimeric and multimeric POX blocks, such as, star-branched and comb-branched polymers.

Symmetrically Branched (SB) Polymers (SBP) and Asymmetrically Branched (AB) Polymers (ABP)

In recent years, dendritic polymers, including Starburst dendrimers (or Dense Star polymers) and Combburst dendrigrafts (or hyper comb-branched polymers), have been developed for a variety of applications ("Dendritic Molecules" ed. by Newkome et al., VCH, Weinheim, 1996 and "Dendrimers and Other Dendritic Polymers" ed. by Frechet & Tomalia, John Wiley & Sons, Ltd., 2001). Those polymers exhibit: (a) a well-defined core molecule, (b) at least two concentric dendritic layers (generations) with symmetrical (equal) branch junctures and (c) exterior surface groups, as described in U.S. Pat. Nos. 4,435,548; 4,507,466; 4,568,737; 4,587,329; 5,338,532; 5,527,524; and 5,714,166, and the references cited therein.

SB dendrimers also are distinctively different from the previously prepared AB dendrimers (U.S. Pat. Nos. 4,289,872; 4,360,646; and 4,410,688 of Denkewalter) which possess asymmetrical (unequal) branch junctures.

Both types of dendrimers can be produced by repetitive protecting and deprotecting procedures through either a divergent or a convergent synthetic approach. Since SB and AB dendrimers utilize small molecules as building blocks for the core and the branches, the molecular weights of such dendrimers often are precisely defined. In the case of lower generation molecules, a single molecular weight dendrimer often is obtained.

Similar to dendrimers, Combburst dendrigrafts also are constructed with a core and concentric layers with symmetrical branches through a stepwise synthetic method. In contrast to dendrimers, Combburst dendrigrafts or polymers are generated with monodisperse linear polymeric building blocks (Tomalia, U.S. Pat. No. 5,773,527 and Yin, U.S. Pat. Nos. 5,631,329 and 5,919,442). Moreover, the branch pattern also is different from that of dendrimers. For example, Combburst dendrigrafts form branch junctures along the polymeric backbones (chain branches) while Starburst dendrimers often branch at the termini (terminal branches). Due to the utilization of living polymerization techniques, the molecular weight distribution ($M_w/M_n$) of such polymeric building blocks (core and branches) often is narrow. As a result, Combburst dendrigrafts, produced through a graft-on-graft process, are rather well defined with an $M_w/M_n$ often less than 1.2.

Although possessing well controlled molecular architecture, such as, well defined size, shape and surface functional groups, both dendrimers and dendrigrafts can be produced only through a large number of reiteration steps, making such useful only for academic pursuits rather than large scale commercial applications.

Dendrimers and dendrigrafts can serve as carriers for bioactive molecules, as described in U.S. Pat. Nos. 5,338,532; 5,527,524; and 5,714,166 of Tomalia for dense star polymers and U.S. Pat. No. 5,919,442 of Yin for hyper comb-branched polymers. The surface functional groups and interior void spaces of those molecules have been suggested as a basis for the carrier property, for example, due to the well-controlled, symmetrical dendritic architecture with predictable branching patterns (either symmetrical termini or polymeric chain branching) and molecular weight.

The preparation of regular (reg) asymmetrically branched polymer (reg-ABP) made of polylysine has been described, as illustrated in U.S. Pat. Nos. 4,289,872; 4,360,646; and 4,410,688.

The synthesis and mechanisms of random (ran) asymmetrically branched polymers (ran-ABP), such as, made of polyethyleneimine (PEI), have been described (see Jones et al., J. Org. Chem. 9, 125 (1944), Jones et al., J. Org. Chem. 30, 1994 (1965) and Dick et al., J. Macromol. Sci. Chem., A4 (6), 1301-1314, (1970)).

The synthesis and characterization of ran-ABP, such as made of POX, for example, PMOX or PEOX, have been described by Litt (J. Macromol. Sci. Chem. A9(5), pp. 703-727 (1975)) and Warakomski (J. Polym. Sci. Polym. Chem. 28, 3551 (1990)).

Randomly branched PEOX has been utilized to physically encapsulate protein molecules (U.S. Pat. No. 6,716,450). However, such an approach was not designed for the direct, covalent linking of ABP with bioactive materials for bioassays and drug delivery applications.

Polymer-Bioactive Material (BM) Compositions

Polymer-bioactive material (BM) compositions, such as, PEG or polyethyleneoxide (PEO)—drug compositions, including directly or indirectly linked conjugates, or physical mixtures of PEG/PEO and drug are known. Although less extensively studied, POX—drug compositions also have been reported, including a linear polymer drug composition, such as those described in Mero et al. in J. Contr. Rel. 125 (2008)87-95 and Viegas et al., Bioconj. Chem. 2011, 22, 976-986, as well as dendritic polymer drug compositions, such as those described by Yin in U.S. Pat. No. 5,919,442.

Special protective chemistries were used during the termination step (Hsiue, Bioconj. Chem. 2006, 17, 781-786, U.S. Pat. No. 7,943,141, US Pub. No. 2011/0123453 and Zhang, et al., Macromol. 2009, 42(6)2215-2221). However, none of those approaches utilized an unprotected, multifunctional small terminating molecule for the in situ functionalization of linear POX polymers, which can significantly reduce production costs.

Assays and Microarrays

Since completion of the human genome project, it has become evident that elucidation of biological pathways and mechanisms at the protein level can be as important as studies at the genetic level because the former is more closely associated with disease and disease states, as well as the treatment thereof. With that strong demand, a new forum called proteomics developed and that art is a major focus of industrial and academic pursuits.

Currently, three major research areas of proteomics studies include drug discovery, high throughput screening and validation of new protein targets and drug leads. Tools include two dimensional (2-D) gel electrophoresis, mass spectrometry, and more recently, protein microarrays. In contrast to the lengthy 2-D gel procedures and tedious sample preparation (primarily separations) involved in mass spectrometry analysis, protein microarrays provide a quick, generally simple and low cost method to screen large amounts of proteins and the functions thereof. Therefore, microarrays are developing as desirable tools in proteomics.

However, protein-based microarray technology is far less developed than is gene microarray technology. The construction of a protein/antibody chip presents daunting challenges not encountered in the development of classical immunoassays or of DNA chips. For example, proteins are more sensitive to the environment than are nucleic acids. The hydrophobicity of many membrane, glass and plastic surfaces can cause protein denaturation destroying the structure and/or function thereof thereby rendering a protein reagent structurally and/or functionally inactive, which can result in lower assay sensitivity and higher signal-to-noise ratios. In other words, to construct a protein microarray, at least three issues must be addressed, protein denaturation, protein immobilization and protein orientation.

For example, a protein molecule often folds into a three-dimensional (3-D) structure in solution for and to maintain biological activity. On interaction with different solid surfaces, for example, during immobilization of proteins onto membranes, glass slides or micro/nanoparticles, the 3-D structure of the protein molecule often collapses thereby often destroying biological activity or at least functional structures. In addition, proteins often do not have the ability to adhere onto different surfaces.

To immobilize a protein on a surface, direct covalent linking reactions or electrostatic interactions (physical adsorption) often are employed. But, heterogeneous chemical reactions often are incomplete yielding undesired side products (i.e. incomplete modification of surfaces) and in some cases, also partially denatured proteins during different reaction stages.

Electrostatic interaction relies heavily on the isoelectric points of the proteins, as well as the pH of the buffer solutions.

Both approaches tend to yield irreproducible results due to the complexity of those procedures. Lot-to-lot reproducibility is, therefore, very poor.

As a result, there is interest in modifying solid substrates, but not the protein molecule, to obtain surfaces carrying biologically active protein. A variety of polymers, including PEI polymers, have been utilized as coating materials to alter the characteristics of solid surfaces for the construction of protein arrays, Wagner et al., U.S. Pat. No. 6,406,921.

SUMMARY

In one aspect, the present invention is directed to terminating a reactive end of a polyoxazoline (POX) polymer with an excess of a multi-functional small molecule with an unprotected amino or imino group so that a one-to-one adduct (one polymer per terminating molecule) can be formed. For example, a POX polymer can comprise the following configuration: Initiator ($I_n$)—POX (P)—End Group ($E_m$), where m and n each is ≥1. On purification, for example, solvent precipitation and/or dialysis, the purified amino-end functionalized (—$NH_2$) or imino-end functionalized (—NH—) POX can be further linked to a pharmaceutically active agent (PAA) through additional linkers to form a covalently linked composition for diagnostic and/or therapeutic uses.

Suitable linker molecules include carbodiimidazole (CDI) or a partial CDI-functionalized molecule (e.g., a reaction product between a CDI and an OH-functionalized molecule or a bioactive material (BM)), glycidol, succinic anhydride, acrylic ester, amidoamine, linear or branched polyamidoamine, acrylamide or an N-hydroxysuccinimide (NHS)-containing heterofunctional molecule to produce a POX-BM composition or a POX polymer with different functional groups, such as, —OH, —COOH, —COONa, ester, amide, maleimide or —SH that can be linked with a BM. In other words, a BM can be linked to the functionalized POX polymers either directly or indirectly through the functional groups.

In another aspect, in embodiments, a biological material, a bioactive material, a pharmaceutically active agent and the like can be complexed with the polymer of interest without a formal reaction resulting in a covalent bond, instead mere mixing of the polymer with the a biological material, a bioactive material, a pharmaceutically active agent and the like results in a physical relationship between same and a polymer of interest such that the two entities demonstrate a coordinated presence. Hence, such a composition without a covalent bond of a biological material, a bioactive material, a pharmaceutically active agent and the like and a polymer of interest has the same properties and functions as other compositions of interest.

In another aspect of the invention, the initiator moiety (I) incorporated into POX polymers may include various functional/protected functional groups. On reaction/deprotection, a second functional group at the initiator end, particularly with a different functionality as that of the end group previously functionalized, can be formed at the initiator end, which can be used for the attachment of an additional BM on the same polymer. For example, in addition to the BM already attached to a POX at the reactive chain end, an additional BM also can be attached to the same polymer at the initiator end, if the POX utilized is linear. If the POX is branched, multiple BM molecules can be attached to the same polymer at the multiple initiator ends. In addition, due to the stepwise reaction approach, not only the same but different BM molecules can be attached to the same POX polymer at the initiator and reactive chain ends. Such a differentiated POX can be useful in linking different kinds of BM molecules, and at varying ratios.

Accordingly, various other functional groups can be introduced at the initiator end of the POX polymer in addition to at the terminator end. The functional groups include, but are not limited to, ethyl bromoacetate, methyl bromoacetate, tert-butyl bromoacetate, propyl bromoacetate, benzyl bromoacetate, sulfur-containing compounds, such as, 2-(p-toluenesulfonyloxy)ethyl disulfide (TOEDS), (chloromethyl) methyl disulfide, bis(iodomethyl)methyl disulfide and 2-bromoethyl disulfide, silicon-containing compounds, such as, (3-chloropropyl)triethoxysilane, (3-bromopropyl) trimethoxysilane and (3-iodopropyl)trimethoxysilane and protected groups for amines or imines, such as, those comprising a carboxybenzyl group, a p-methoxybenzyl carbonyl group, a tert-butyloxycarbonyl group and a 9-fluorenylmethyloxycarbonyl (FMOC) group; and so on.

For example, TOEDS, a difunctional initiator, can be utilized to initiate the polymerization of oxazoline monomers at both ends. On termination, for example, with a large excess of ethylene diamine (EDA), a POX polymer with amino and imino functional groups at both chain ends can be produced. The chain ends further can be linked with any of a plurality of bioactive materials, such as, small molecule drugs, such as, gemcitabine, camptothecin, paclitaxel and so on, either directly or indirectly through covalent linkages. When the reagents comprise a disulfide bond, addition of a reducing agent, such as, dithiothreitol (DTT), can cleave that bond to generate a sulfhydryl-functionalized POX polymer-bioactive material composition. The sulfhydryl group then can be linked, for example, with a maleimide-functionalized targeting molecule, such as, peptide, protein, such as, antibody, sialic acid, one member of a binding pair and so on to provide a differentiated POX polymer composition with one end linked with any of a plurality of bioactive materials, such as, small molecule drugs, and the other end linked with at least a targeting molecule, such as, peptide, protein, such as, antibody, sialic acid and so on. Various differentiated POX compositions, including, but not limited to, biologically active molecules to generate, such as, BAM-POX-PAA, $BAM_1$-POX-$BAM_2$, $PAA_1$-POX-$PAA_2$ and so on are contemplated. BAK and $BAM_2$ represent different biologically active materials, while $PAA_1$ and $PAA_2$ indicate different pharmaceutically active agents. In addition to different BAM, PAA and binding pairs that can be attached to the same POX polymer, different ratios of each of a BAM, PAA and binding pair also can be linked to the same polymer.

In some embodiments, a functionalized polyoxazoline polymer is provided, wherein said polymer comprises the formula: $I_n$—P-L-M-B, wherein I is an initiator, n≥1, P is a polyoxazoline polymer, L is a first linker comprising at least two amine groups, at least two imino (—NH—) groups or at least an amino group and an imino group, wherein said first linker is attached to said polymer by one of said at least two amine groups, at least two imino (—NH—) groups or at least an amino group and an imino group, M is a second linker and B is a bioactive material.

BRIEF DESCRIPTION OF THE FIGURES

The following description of the figures and the respective drawings are non-limiting examples that depict various embodiments that exemplify the present invention.

DETAILED DESCRIPTION

Figure 1:
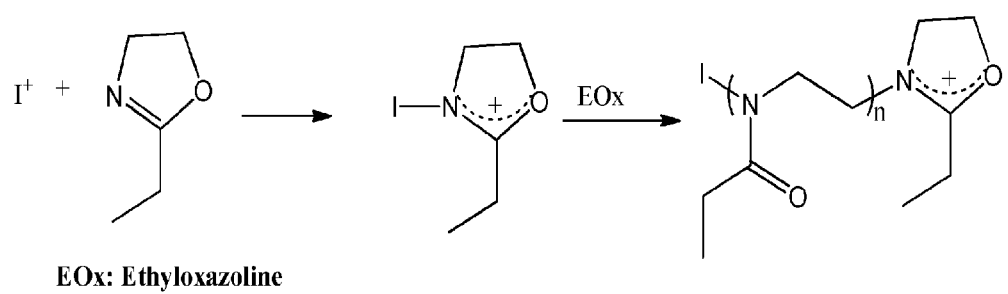
FIG. 1 depicts a poly(2-ethyloxazoline) (EOx, also, EOX) (PEOX or PEOx) polymer produced through a cationic ring-opening polymerization process. The initiator, I, can comprise different functional groups, such as, an alkyl, an aryl, an ester, an amide, a sulfur-containing group, a silica-containing group, a protected amine, a protected imine and so on. n is the number of repeat units in the polymer which is dictated by reaction conditions and as a design choice.
Figure 2:
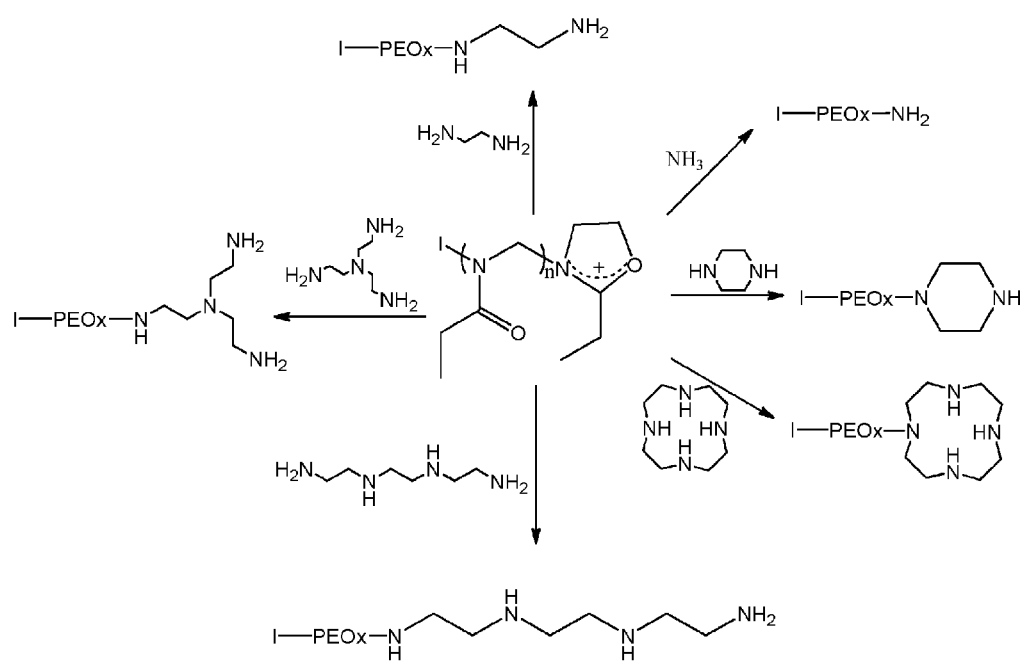
FIG. 2 depicts termination of a reactive poly (2-ethyloxazoline) polymer chain end with an excess of various small molecules with multifunctional, unprotected amino or imino groups.
Figure 3:
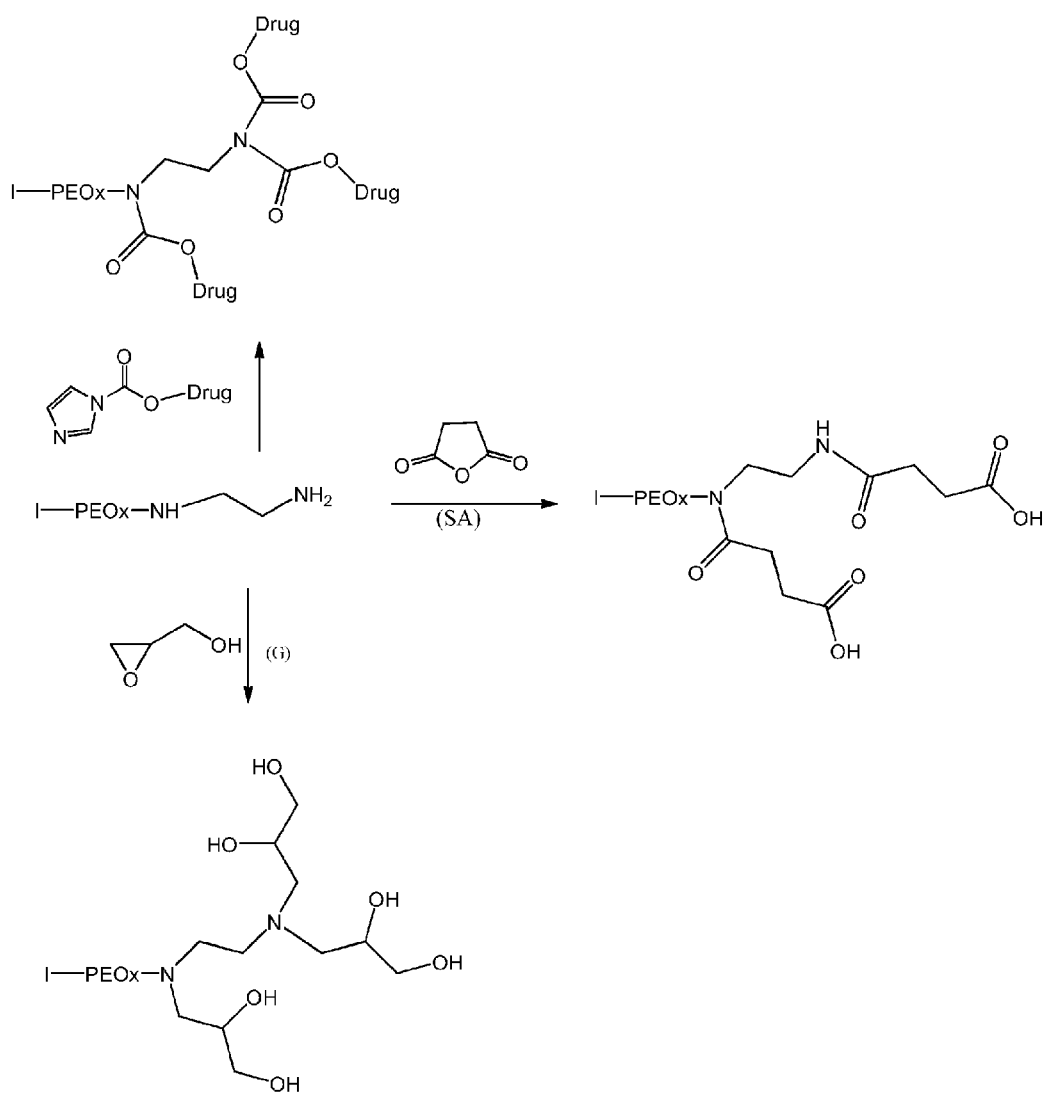
FIG. 3 depicts reaction of amino-terminated or imino-terminated poly (2-ethyloxazoline) with additional linker groups, including glycidol (G), succinic anhydride (SA) or an imidazole-drug ester.
Figure 4:
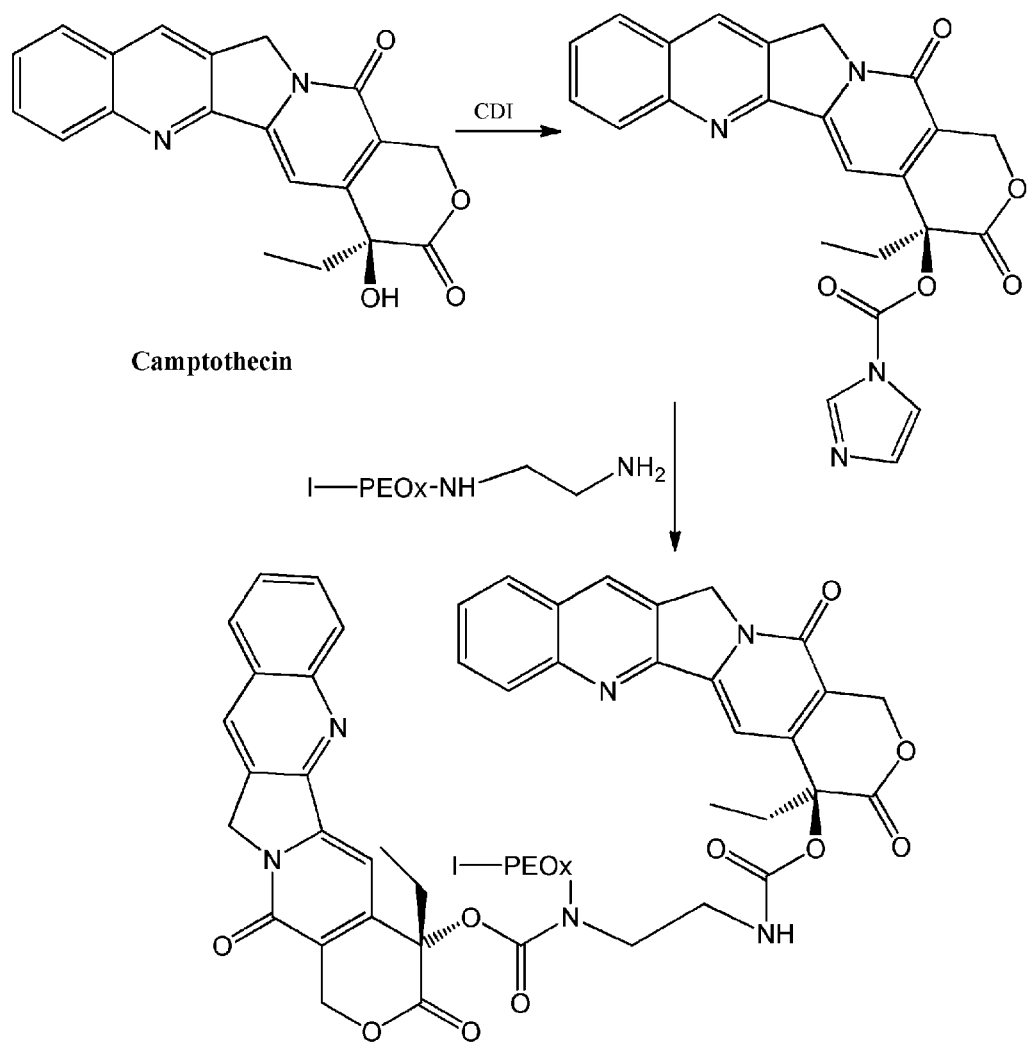
FIG. 4 depicts an example for the synthesis of a poly (2-ethyloxazoline) and camptothecin composition.
Figure 5:
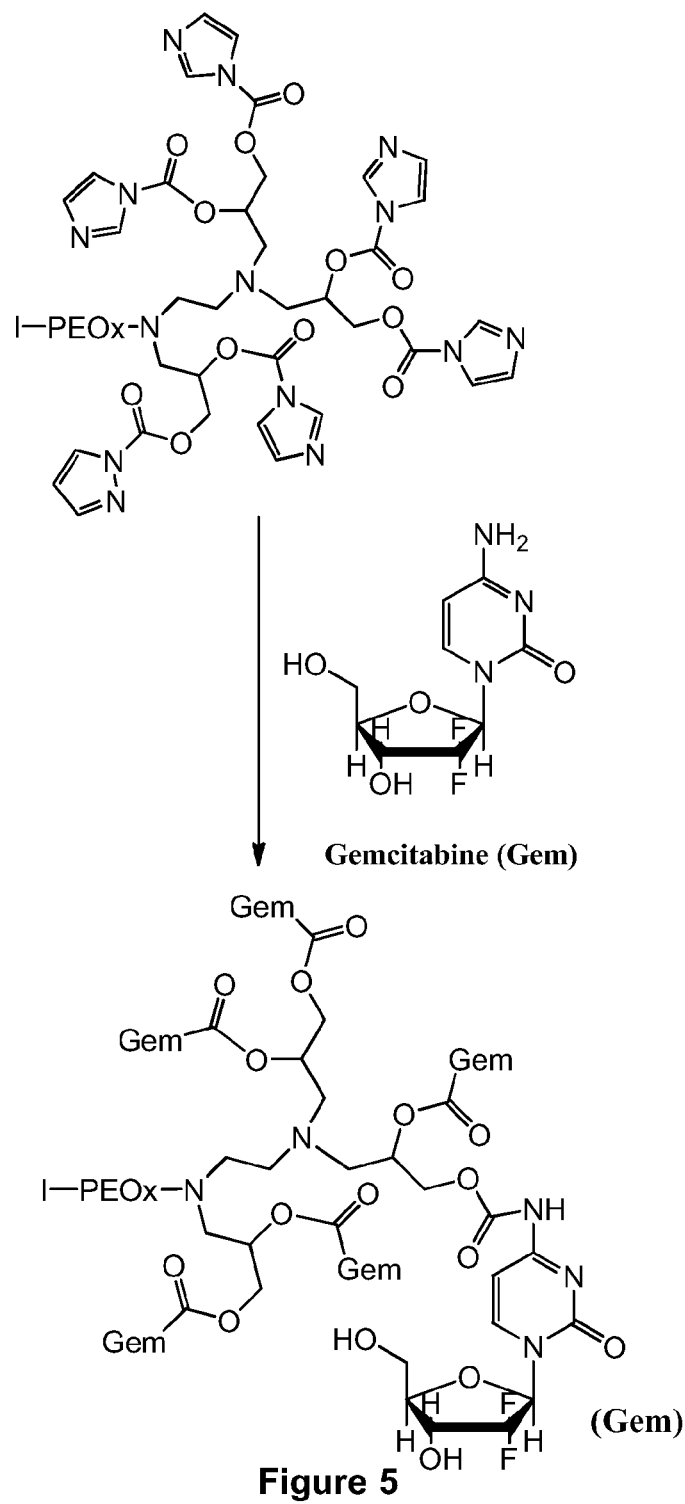
FIG. 5 depicts an example for the synthesis of a poly (2-ethyloxazoline) and gemcitabine composition.
Figure 6:
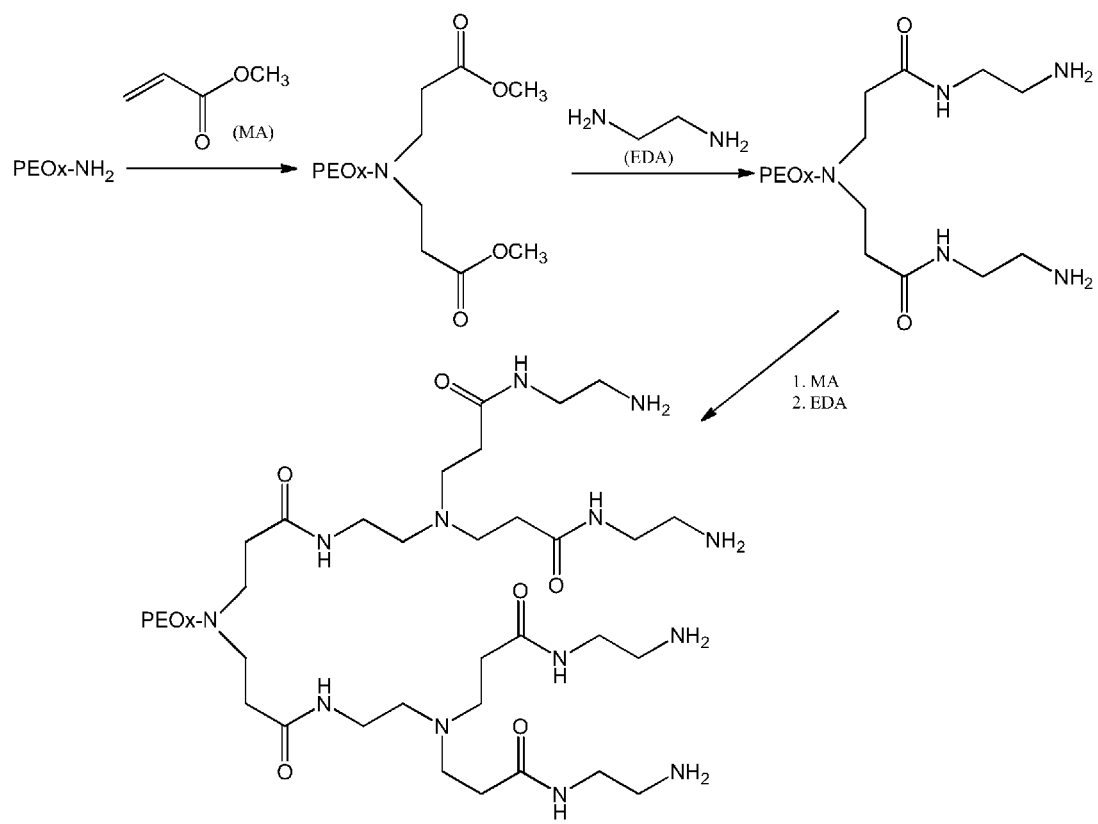
FIG. 6 depicts the synthesis of a modified poly (2-ethyloxazoline) polymer prior to linking with a bioactive material. MA is methacrylate. EDA is ethylenediamine. PEOx is PEOX.
Figure 7:
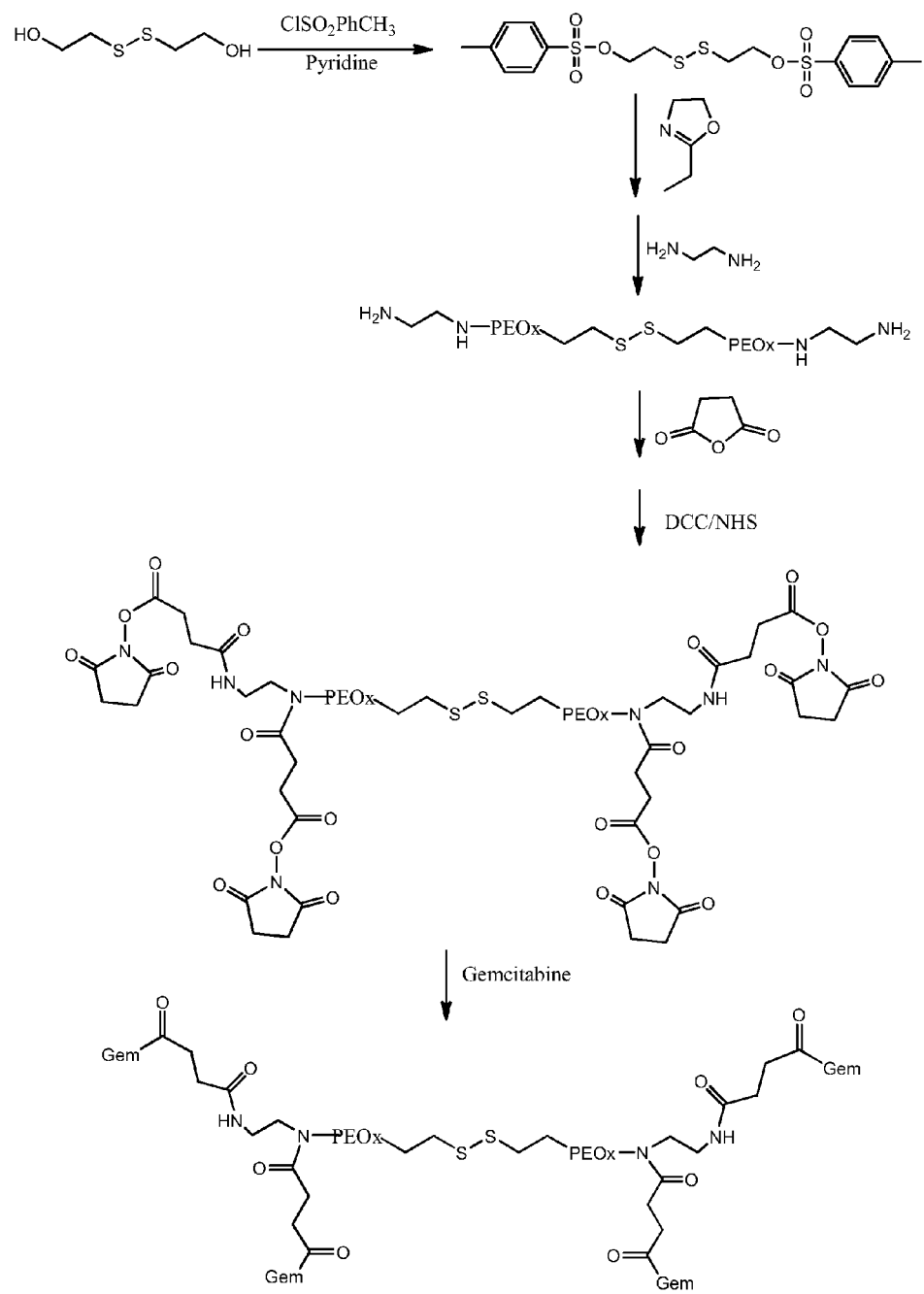
FIG. 7 depicts the synthesis of a PEOX-gemcitabine composition with an S—S linkage within the PEOX polymer. The initiator is cleavable. $ClSO_2PhCH_3$ is p-toluenesulfonyl chloride. NHS is N-hydroxysuccinimide. DCC is dicyclohexylcarbodiimide. In the second reaction step, EOX is added. In the fourth reaction step, SA is added.
Figure 8:
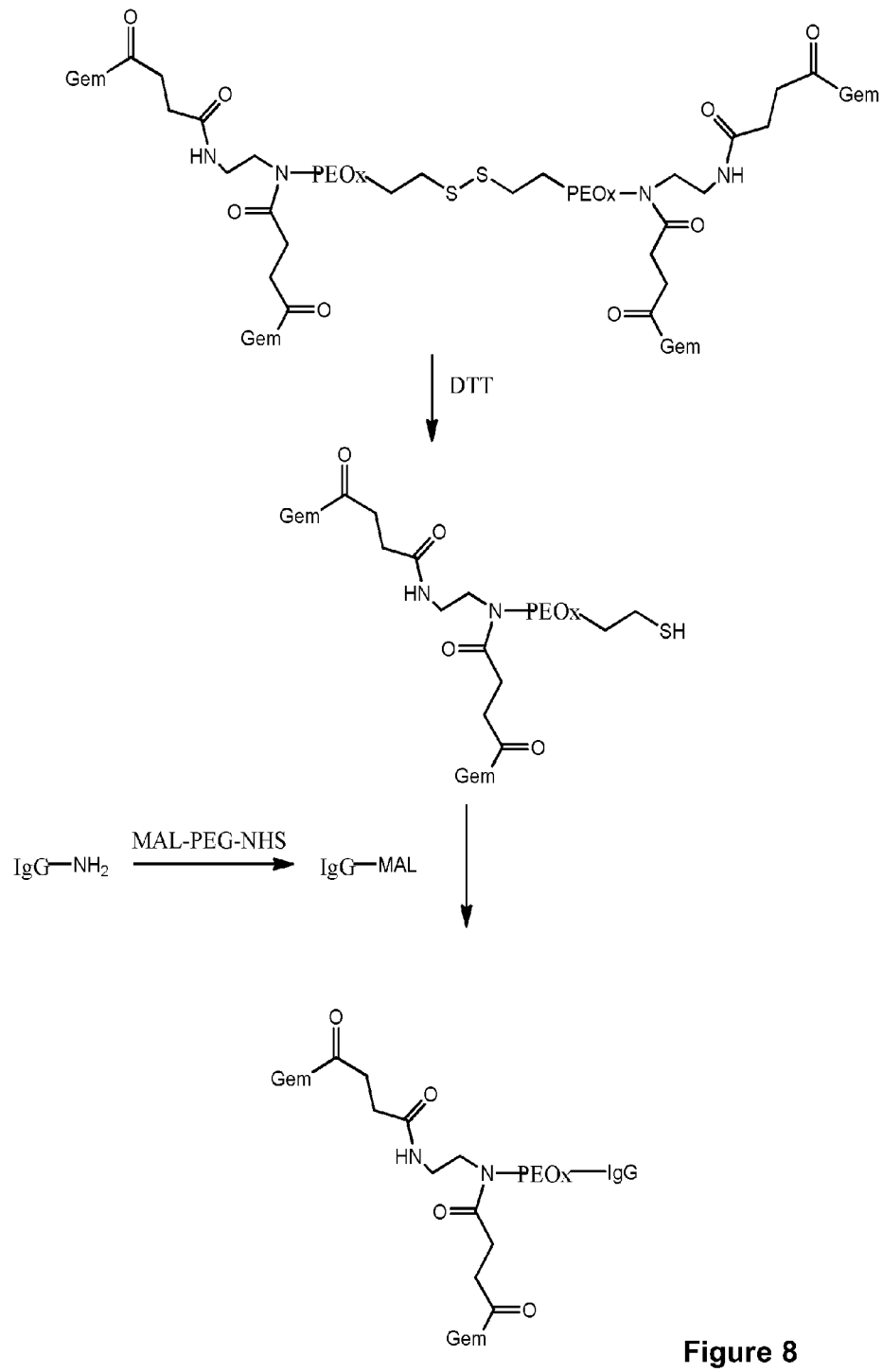
FIG. 8 depicts the synthesis of an antibody (IgG)-gemcitabine composition through a PEOX polymer linker. DTT is dithiothreitol. MAL is maleimide. PEG is polyethyleneglycol.
Figure 9:
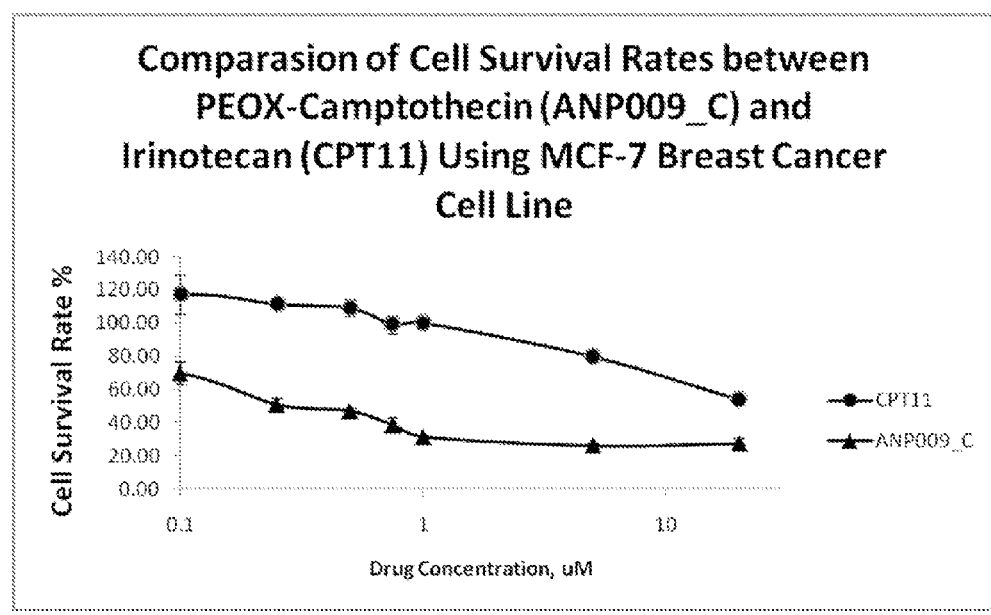
FIG. 9 depicts comparative data on cancer cell killing rates between PEOX-camptothecin and Irinotecan (CPT11), a semisynthetic analog of camptothecin, using MCF-7, a breast cancer cell line.
Figure 10:
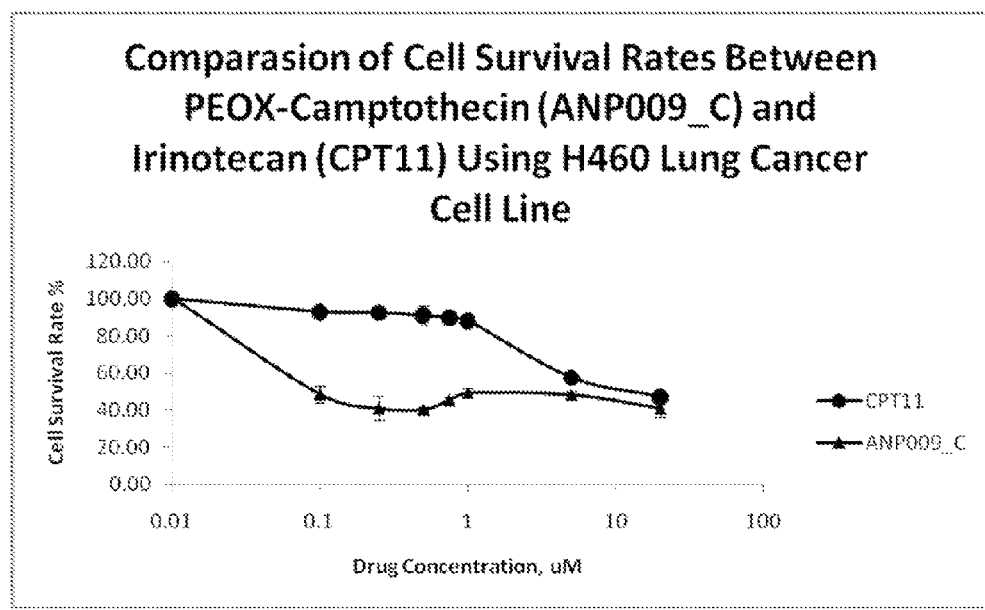
FIG. 10 depicts comparative data on cancer cell killing rates between PEOX-camptothecin and Irinotecan (CPT11) using H460, a lung cancer cell line.

As used herein, an, "alkyl group", comprises aliphatic compounds, which can be linear or branched chains, can comprise one or more non-aromatic rings and so on. The alkyl can comprise one or more saturated bonds or can be unsaturated. Also, the alkyl can comprise one or more pendant groups, functional groups, modifications and the like, which can include other elements, such as, oxygen, nitrogen, sulfur, iodine, bromine or chlorine, or can contain a polar group, such as hydroxyl or amine or a non-polar group, such as, a hydrocarbon, such as, an aliphatic group or an aromatic group, which also can be substituted.

As used herein, an, "aryl group," comprises a hydrocarbon with alternating double and single bonds between carbons, that is, an aromatic structure. An aryl can comprise multiple aromatic rings, which may be fused or joined, and which can be substituted. An aryl also can comprise a heterocyclic compound, such as, an unsubstituted and a substituted furan or pyridine.

As used herein, an, "ester," is a chemical compound derived by reacting an oxoacid, such as, a carboxyl acid, with a hydroxyl compound, such as, an alcohol or phenol. Esters are usually derived from an inorganic acid or organic acid in which at least one —OH (hydroxyl) group is replaced by an —O-alkyl (alkoxy) group, and most commonly from carboxylic acids and alcohols. That is, esters are formed by condensing an acid with an alcohol.

As used herein, an, "amide," is an organic compound that contains the functional group consisting of a carbonyl group (R—C=O) linked to a nitrogen atom (N).

As used herein, a, "sulfur-containing compound," is one which contains one or more reactive sulfur atoms. The compound can be 2-(p-toluenesulfonyloxy)ethyl disulfide (TOEDS), (chloromethyl) methyl disulfide or bis(iodomethyl)methyl disulfide, 2-bromoethyl disulfide, for example.

As used herein, a, "silica-containing compound," is one containing at least one silicon atom. The compound can be (3-chloropropyl)triethoxysilane, (3-bromopropyl)trimethoxysilane or (3-iodopropyl)trimethoxysilane, for example.

As used herein, "protective groups for an amine or an imine," or a, "protected amine or protect imine," is an amine or imine which comprises a carboxybenzyl group, a p-methoxybenzyl carbonyl group, a tert-butyloxycarbonyl group, a 9-fluorenylmethyloxycarbonyl (FMOC) group and so on.

Herein, B, BM and BAM can be used as synonyms and can be used interchangeably. A B can comprise a PAA.

As known, a polymer comprises a number of component monomers which may be the same or different. As known, the molecular formula of a polymer can be denoted by naming the one or more monomers and with a subscript indicating the number of that monomer in the polymer. As used herein, "n," is not meant to relate to any particular sized polymer. Instead, n is meant to indicate a polymer and the value of n is a design choice, based, for example, on the intended use.

Binding Pairs

A member of a binding pair can include, for example, an antibody or an antigen-binding portion thereof, an antigen, an avidin/streptavidin/neutravidin, anti-streptavidin, a biotin, a dinitrophenol (DNP), an anti-DNP antibody, a digoxin, an anti-digoxin antibody, a digoxigenin, an anti-digoxigenin antibody, a hapten, an anti-hapten antibody, a polysaccharide, a polysaccharide binding moiety, such as a lectin, a receptor, a fluorescein, an anti-fluorescein antibody, a complementary DNA, an RNA, an antibody and an $F_c$ receptor and so on that are complementary and bind each other or one binds the other.

Pharmaceutically Active Agents (PAA)-Small and Large Molecule Drugs

Small molecule drugs are defined as those with a molecular weight that can be less than about 1,000 Da, while large molecule drugs are larger sized and also can comprise biologicals or are derived from a biological molecule. For example, a large molecule drug can include a natural biopolymer, such as, a polypeptide (e.g., a protein), a nucleic acid (e.g., DNA or RNA), a polysaccharide, a lipid and so on, as well as combinations thereof, such as, a glycolipid, a glycoprotein, a lipoprotein and so on, and can include synthetic biopolymers, such as, an aptamer, a peptide nucleic acid (PNA) and so on.

Examples of pharmaceutically active agents (PAA), such as, drugs, include, but are not limited to, chlormethine, chlorambucil, busulfan, thiotepa, cyclophosphamide, estramustine, ifosfamide, meclilorethamine, melphalan, uramustine, lonuistine, streptozotocin, dacarbazine, procarbazine, temozolainide, cisplatin, carboplatin, oxaliplatin, satraplatin, (SP-4-3)-(cis)-aminedichloro-[2-methylpyridine]-platinum (II), methotrexate, permetrexed, raltitrexed, trimetrexate, camptothecin, camptothecin derivatives (such as, irinotecan, topotecan etc.), cladribine, chlorodeoxyadenosine, clofarabine, fludarabine, mercaptopurine, pentostatin, thioguanine, azacitidine, capecitabine, cytarabine, edatrexate, floxuridine, 5-fluorouracil, gemcitabine, troxacitabine, bleomycin, dactinomycin, adriamycin, actinomycin, mithramycin, mitomycin, mitoxantrone, porfiromycin, daunorubicin, doxorubicin, liposomal doxorubicin, epirubicin, idarubicin, valrubicin, phenesterine, tamoxifen, piposulfancamptothesin, paclitaxel, docetaxel, taxotere, vinblastine, vincristine, vindesine, vinorelbine, amsacrine, etoposide, teniposide, fluoxymesterone, testolactone, bicalutamide, cyproterone, flutamide, nilutamide, aminoglutethimide, anastrozole, exemestane, formestane, letrozole, dexamethasone, prednisone, diethylstilbestrol, fulvestrant, raloxifene, toremifene, buserelin, goserelin, leuprolide, triptorelin, medroxyprogesterone acetate, megestrol acetate, levothyroxine, liothyronine, altretamine, arsenic trioxide, gallium nitrate, hydroxyurea, levamisole, mitotane, octreotide, procarbazine, suramin, thalidomide, methoxsalen, sodium porfimer, bortezomib, erlotinib hydrochloride, gefitinib, imatinib mesylate, semaxanib, adapalene, bexarotene, trans-retinoic acid, 9-cis-retinoic acid, N-(4-hydroxyphenyl) retinamide, tiuxetan, ozogamicin, glargine and so on, as well as derivatives thereof.

Large molecule drugs include, for example, proteins, such as, enzymes, such as, L-asparaginase, antibodies and anti-gen-binding portions thereof, such as, alemtuzumab, bevacizumab, cetuximab, ibritumomab, rituximab, trastuzumab, gemtuzumab and tositumomab, cytokines, such as, interleukins, interferon α2a, interferon α and granulocyte colony stimulating factor (GCSF), peptide hormones, such as, insulin, glucagon, glucagon like peptide-1, erythropoietin, follicle stimulating hormone and so on, ligands of cell surface receptors, lectins, nucleic acids, such as siRNA's, ribozymes, antisense nucleic acids, naked nucleic acids and so on, viruses, virus-like particles and the like. Examples include Ecallantide.

Additional examples include recombinant blood factors, such as, Factor III, antihemophilic factor, Factor VIII, antithrombin, thrombin, Factor VIIa, Factor IX; tissue plasminogen activator, such as, TNK-tPA, tenecteplase and alteplase, including truncated forms thereof, such as, reteplase, hirudin, protein C and so on; recombinant hormones, such as, insulin, such as, insulin detemir, a long-acting insulin analog, insulin glulisine, a rapid-acting insulin analog and insulin glargine (another long-acting insulin analog); human growth hormone, also known as somatropin, follicle-stimulating hormone, such as, the α subunit thereof, such as, corifollitropin α, glucagon like peptide-1, parathyroid hormone, and truncated forms thereof, such as, terpiparatide, B-type natriuretic peptide, calcitonin, luteinizing hormone, hCG, TSH, glucagon and so on; recombinant growth factors, such as, erythropoietin, such as, epoetin θ, erythropoietin a and epoetin ζ, long acting analogs thereof, such as, darbepoetin α; colony stimulating factors, such as, GM-CSF and G-CSF, insulin-like growth factor (IGF), a complex of IGF and IGF binding proteins, such as, mecasermin rinfabate, keratinocyte growth factor, platelet-derived growth factor and so on; recombinant cytokines, such as, interferons and interleukins, such as, interferon α, IFN-α-2b, interferon β, interferon-β-1B, IFN-β-1a, IL-11, IL-2, IFN-γ1b and so on; recombinant vaccines, such as those for Hepatitis B, papillomavirus (HPV), cholera toxin B subunit, OspA, a lipoprotein found on the surface of *B. burgdorferi*), pertussis toxin and so on; monoclonal antibody and antigen-binding portions thereof, made to any antigenic entity as known in the art, such as, denosumab, tocilizurmab, besilesomab, ofatumumab, canakinumab, catumaxomab, golimumab, steknumab, ranibizumab, eculizumab, panitumumab, natalizumab, omalizumab, ibritumonmab, cetuximab, efalizumab, adalimumab, tositumomab, infliximab, palivizumab, daclizumab, votumumab, basiliximab, sulesomab, igovomab, abciximab and so on; other recombinant biologics, such as, bone morphogenetic proteins, such as, BMP-7 and BMP-2) and so on; recombinant enzymes, such as, α glucosidase, glucocerebrosidase, iduronate-2-sulfatase, N-acetylgalactosidase, 4-sulfatase, β-glucocerebrosidase, DNase, hyaluronidase, α-galactosidase, α-L-iduronidase, urate oxidase and so on; oligonucleopeptides; and so on, as well as combinations thereof, such as, rilonacept (a dimeric fusion protein of the extracellular (EC) domain of the IL-1 receptor and the $F_c$ portion of an IL-1 IgG-1), romiplostim (a dimeric fusion protein with each monomer consisting of two thrombopoietin receptor-binding domains and the $F_c$ region of an IgG-1), Abatacept (an immunoglobulin fused to the EC domain of CTLA-4), alefacept (containing the $F_c$ portion of an antibody and a portion of CFA-3) and so on.

Biologically Active Molecules (BAM)

In addition to binding pairs, certain large molecule drugs and PAA's described above, some additional examples of a BAM include, but are not limited to, interleukins, interferons, $CD_4$ and other CD molecules, including agonists and antagonists thereof, $F_c$ receptor, acetylcholine receptor (AChR), T cell receptor, hormone receptors, such as, an insulin receptor, tumor necrosis factor, granulocyte-macrophage colony stimulating factor, antibodies and antigen-binding fragments thereof, such as, $F_{ab}$ and scAb, phage, phage fragments, sugars containing sialic acid residues, cell targeting peptides, DNA fragments, RNA fragments, hormones, such as, insulin and hCG, enzymes, sialic acid, polysaccharides, lectin, porphyrins, nucleotides, viruses, viral fragments and so on, other receptors and the like.

Bioactive Materials (BM)

In the disclosure, bioactive materials comprise binding pairs, a BAM, a PAA, small and large molecule drugs and any other biologically active or related molecules.

Polyoxazoline-Bioactive Material Composition

POX-BM compositions of interest can have the following formula:

$I_n$—P-L-M-B, wherein I is an initiator moiety and n≥1. I can comprise an alkyl, an aryl, an ester, an amide, a sulfur-containing compound, a silica-containing compound, a protected amine or a protected imine;

P is a POX polymer;

L is a linker comprising at least two amine groups, at least two imino (—NH—) groups or at least an amino group and an imino group, wherein said first linker is attached to said polymer by one of said at least two amine groups, at least two imino (—NH—) groups or at least an amino group and an imino group, in embodiments, said linker can comprise a small molecule comprising plural amino or imino (—NH—) groups, wherein said small molecule can comprise either an entire or a portion of ammonia, ethylenediamine (EDA), piperazine, 1,4,7,10-tetraazacyclododecane (cyclen), tris(2-aminoethyl)amine (tren), 4-(aminomethyl)piperidine, hexamethylenediamine, 1,3-diaminopropane, triethylenetetramine, 2,2'-(ethylenedioxy)bis(ethylamine), 1,11-diamino-3,6,9-trioxaundecane, diethylenetriamine, tris(2-aminoethyl)amine, 1,8-diaminooctane and so on; and M is an additional linker, comprising, for example, a CDI or a partial CDI-functionalized molecule (e.g., an imidazole-PAA ester), glycidol, succinic anhydride, acrylic ester, amidoamine, linear or branched polyamidoamine, acrylamide and/or a heterofunctional molecule, with one end of the heterobifunctional molecule activated with, for example, N-hydroxysuccinimide (NHS) or an aldehyde functional group, for reaction with the L linker. The other end of the heterobifunctional molecule comprises a reactive group to facilitate reaction with the B entity, such as, a —OH, —COOH, —COONa, an ester, an amide, a maleimide or an —SH group. Alternatively, B also can be physically mixed with $I_n$—P-L-M to form a polyoxazoline-bioactive material composition without the need for a specific reaction to form a covalent bond between B and the remainder of the composition.

A partial CDI-functionalized molecules comprises a reaction product between a CDI and, for example, an OH-functionalized molecule or a bioactive material (BM).

B is a bioactive material linked with said polymer through either a hydrolytically stable or an unstable linkage. Alternatively, in embodiments, B may be associated with the remainder of a composition of interest in the absence of a formal linkage as described herein. Hence, mere mixing of B with I—P-L-M yields a composition of interest.

Therefore, I, L and M can possess the same or different functional groups. When possessing different functional groups, one set of BM's can be attached at the L end, while a different set of BM's can be linked to an initiator end. For example, one can link a small molecule drug moiety at the L end while an antibody can be attached to the initiator, I, end(s) to form an antibody/drug conjugate (ADC). Alternatively, an antibody can be attached at the L end while the small drug molecule can be linked to the initiator I end(s) to also form an ADC at the same or at different ratios as the previous method. Other combinations may include linking two different BM molecules or two different PAA's at the I and L ends, respectively.

In addition, the linkers can be tailored to produce either hydrolytically stable or unstable chemical linkages so that various delivery systems can be generated, depending on the need for controllable B release rates. Readily cleavable linkages include, but are not limited to, an anhydride bond, an S—S (sulfur-sulfur bond) linkage, a peptide bond that can be cleaved by an enzyme and so on.

In another aspect of the invention, the POX can be linear, starbranched, combbranched, dendritically branched or a randomly branched polymer. Said branched or dendritic polymers can either be symmetrically or asymmetrically branched.

In another aspect of the invention, the POX can be a poly (unsubstituted oxazoline) or a poly (substituted oxazoline) polymer. The poly (substituted oxazoline) can be poly (2-methyloxazoline), poly (2-ethyloxazoline), poly (2-propyloxazoline) or poly (2-butyloxazoline).

In another aspect of the invention, the polymer—bioactive material composition can be used for various assay and drug delivery applications.

In another aspect of the invention, the differentiated, that is, comprises a heterofunctional group, POX polymers can be used to produce antibody-BM compositions for assays.

In another aspect of the invention, the differentiated/heterofunctional POX polymers can be used to produce antibody-PAA compositions for targeted drug delivery.

Also, polymer associated with multiple units of BM, and each with different properties and activities, can be used, for example, for targeting or for bridging biological entities, such as, a hormone and a receptor, or two cells. Such compositions may be formulated with acceptable carriers, diluents and additives for use, for example, in biodetection, diagnostics and therapeutics, as known in the medical, environmental, agricultural and physical sciences.

In another aspect of the invention, the said POX polymer can be modified with at least one monomer capable of forming additional branches at a given time so that new material properties can be achieved, wherein the said modified polymer is defined as a modified POX polymer. A suitable monomer can be one carrying plural reactive functional groups, which can be the same or different.

The molecular weight of said polymers can range from about 500 to over 5,000,000; from about 500 to about 1,000,000; from about 1,000 to about 500,000; from about 2,000 to about 100,000.

In one aspect of the invention, said polymer-BM composition can be utilized, for example, for the rapid detection of target molecules of interest, such as, environmental pollutants, chemical and biological warfare agents and so on, as well as for screening for drug targets and leads, and therapeutic drug and therapeutic impact monitoring.

In another aspect of the invention, said polymer-BM composition can be utilized, for example, for the rapid diagnosis of diseases, such as, cancer, pathological states, as well as for monitoring biomarker changes and protein profiling during life stages, clinical trials and therapeutic treatments.

In another aspect of the invention, said polymer-BM composition can be utilized, for example, for the construction of direct sandwich, indirect sandwich, sequential and competition assays. The assays can be used for either biomarker detection, as well as immunogenicity testing, for example, anti-drug antibody detection.

In yet another aspect of the invention, at least one said polymer can be utilized to carry at least one polypeptide to a solid surface generating virtually no denaturation of the at least one polypeptide. The solid surface can include nitrocellulose, paper, other membranes, glass, metal, a silica-containing device, plastic and the like, and can be presented in a variety of forms, such as flat surfaces, such as, sheets, strips and so on, spheres, such as, particles, beads, and so on, and can be used, for example, for the generation of plate microarrays, bead arrays, microarrays or nanoarrays. The bead micro/nanoarrays either can be constructed through the attachment of multiple molecules, such as, polypeptides of a composition of interest on the same micro/nanoparticle or by having a bead carrying only one species of molecule, such as, a polypeptide of a composition of interest, and mixing beads as desired, wherein each bead carries a specific kind or species of molecule, such as, a polypeptide. In addition to detection, the arrays and assays, such as, bead micro/nanoarrays, also can be utilized for rapid, large-scale, high throughput separation of bioactive materials prior to analysis with protein plate microarrays, 2D gels or mass spectrometers, for example.

As known in the art, assays can be presented in a number of formats, often based on, for example, the separation of reagents on a solid phase and in a liquid phase, formation of molecular bridges and detectable reporter molecules. Hence, binding pairs can play a role in such assays, such as, antibodies, receptors, single-stranded nucleic acids, that may bind by base pairing or by other molecular interaction, such as, forming a triplex nucleic acid or an aptamer, and so on.

As known in the art, a binding pair reagent can be labeled with a detectable reporter, or the detectable reporter can be affixed to another reagent, which can be a member of another binding pair, which indirectly detects the target, for example, to the complex of the target and the binding pair thereof or to the binding pair member bound to the target or to the target, for example. Thus, in some embodiments, two members of mutually exclusive binding pairs each bind the target to form a, "sandwich." Often, one binding pair member is affixed to a solid phase and the other binding pair member may carry the reporter. In such assays, signal level correlates directly with target amount.

In other embodiments, an assay can be configured where the target is tasked with competing for binding to a site with a labeled ligand which also is bound by that site. The target and the ligand can be the same. It follows that in such competition assays, the greater the target concentration, the more likely a target will be bound at the site than a labeled ligand. Thus, in such competition assays, signal correlates inversely with target concentration.

The particular configuration and the particular reagents used in an assay are a design choice based on methods known in the art, reagents known in the art and taught herein and the binding reactions that provide the mechanism of the assay.

As a binding pair comprises receptors, lectins, nucleic acids and so on, the reactants of an assay can comprise any such binding pair as a design choice. Hence a binding pair can comprise a receptor and a hormone, a lectin and a molecule comprising the cognate carbohydrate, complementary nucleic acids, nucleic acids that bind in a fashion similar to that of an antibody, such as, an aptamer, and so on. A combination of different types of binding pairs can be employed in an assay. For example, a nucleic acid may bind a target complement thereof. The detecting nucleic acid comprises a nucleoprotein bound thereto. A solid phase may comprise an antibody which specifically binds the nucleoprotein, and so on.

The composites taught herein can be employed in such assays, for example, the initiator can comprise a reporter molecule and B may be a member of a binding pair that directly or indirectly binds the target.

The polymer compositions of interest can be used as drug delivery devices, which can provide bolus delivery, sustained release, delayed release, timed release, enteric coating and various other pharmacological formulations of desired characteristics. Such composite molecules may also be utilized as sensing components in various sensor platforms including, but not limited to, optical, electrical and piezoelectric devices, as well as in microfluidics, and in microelectromechanical systems (MEMS) and nanoelectromechanical systems (NEMS).

The invention now will be exemplified in the following non-limiting examples.

EXAMPLES

Materials

All chemicals were available commercially, such as, methylacrylate (MA), ethylenediamine (EDA), piperazine, cyclen, tris(2-aminoethyl) amine (tren), oligomeric ethyleneimines, methyloxazoline, dimethylformamide (DMF), ethyloxazoline, morpholine, N,N'-carbonyldiimidazole (CDI), 4-(aminomethyl)piperidine and dithiothreitol (DTT) were purchased from Sigma-Aldrich. Symmetrically and asymmetrically branched polymers were prepared according to procedures provided in U.S. Pat. Nos. 4,631,337; 5,773,527; 5,631,329; 5,919,442; and 7,754,500. All of the antibodies were purchased from Sigma-Aldrich, Biodesign or Fitzgerald.

Polymer and Polymer Composite Size Measurement

The size of various polymers and polymer-BM compositions was measured by a size exclusion chromatography and a dynamic light scattering method using a Malvern Zetasizer Nano-ZS Zen3600 particle size analyzer.

Activity Testing

Metabolism in viable cells produces, "reducing equivalents," such as, NADH or NADPH. Such reducing compounds pass electrons to an intermediate electron transfer reagent that can reduce the tetrazolium product, MTS (Promega), into an aqueous, soluble formazan product, which is colored. At death, cells rapidly lose the ability to reduce tetrazolium products. The production of the colored formazan product, therefore, is proportional to the number of viable cells in culture. The CellTiter 96® AQueous system (Promega) is an MTS assay for determining the number of viable cells in culture. A single reagent added directly to the culture wells at the recommended ratio of 20 µl reagent to 100 µl of culture medium was used. Cells were incubated 1-4 hours at 37° C. and then absorbance was measured at 490 nm.

Thus, the cytotoxicity of various polymer-drug compositions of interest, along with commercially available drugs or their derivatives, was tested on different cancer cell lines (from ATCC) including, lung cancer cell lines, H460 and A549, and breast cancer lines, MDA-MB-231 and MCF-7, at concentrations ranging from 0.5 mg/mL to 2.5 ng/mL.

Drug-containing nanoparticles of interest comprising a branched polymer, such as, a POX polymer of interest and a PAA, were at least the same or were more potent at killing cancer cells, particularly at low drug concentrations, than PAA alone.

Synthesis of Alkyl-Modified Random (Ran) Asymmetrically Branched (AB) Poly(2-ethyloxazoline) (PEOX) with Primary Amine Chain End Group The synthesis of $CH_3-(CH_2)_{11}$-PEOX-ABP100 (ABP100 is an arbitrary designation to denote the ratio of asymmetrically branched polymer (ABP) monomer to initiator in the initial reaction mixture. Hence, in the above, there is a 100:1 ratio of EOX to initiator. The following synthesis scheme is provided as a general procedure for the preparation of other compositions of interest.

A mixture of 1-bromooctadecane ($CH_3(CH_2)_{17}Br$) (2.52 g) in 500 ml of toluene was azeotroped to remove water. 2-Ethyloxazoline (100 g) was added dropwise through an addition funnel and the mixture was allowed to reflux between 24 and 48 hours. On completion of polymerization, 12.12 g of EDA were added to the reactive polymer solution to introduce an amine functional group. The molar ratio of polyoxazoline chain end to EDA was about 1 to 20.

N-tert-butyloxycarbonylpiperazine (N-Boc-piperazine) or water (e.g., with 1N $Na_2CO_3$) can be added to terminate the reaction. Morpholine also can be added to the polymer solution to terminate the reaction. The crude product was redissolved in methanol and then precipitated from a large excess of diethyl ether. The bottom layer was redissolved in methanol and dried by rotary evaporation and vacuum to yield an asymmetrically random branched PEOX polymer as a white solid (101 g). Other asymmetrically randomly branched polymers, such as, $C_6$-PEOX (using, for example, 1-bromohexane) ABP20, 50, 100, 200, 300 or 500, $C_{18}$-PEOX (using, for example, 1-bromooctadecane) ABP20, 50, 100, 200, 300 or 500, $C_{22}$-PEOX (using, for example, 1-bromodocosane) ABP20, 50, 100, 200, 300 or 500, etc., were prepared in a similar manner. All the products were analyzed by size exclusion chromatography (SEC) and nuclear magnetic resonance (NMR).

Synthesis of Linear Poly (2-ethyloxazoline) (PEOX) with Primary Amine Chain End Group The synthesis of linear HPEOX100 (H is hydrogen) is provided as a general procedure for the preparation of linear POX with a primary amine chain end group. A mixture of p-toluenesulfonic acid monohydrate (FW=190.22; 1.92 g) in 500 ml of toluene was azeotroped to remove water. 2-Ethyloxazoline (100 g) was added dropwise through an addition funnel and the mixture was allowed to reflux about 6 hours. On completion of the polymerization, 12.12 g of EDA were added to the reactive polymer solution to introduce an amine functional group. The molar ratio of polyoxazoline chain end to EDA was about 1 to 20.

N-tert-butyloxycarbonylpiperazine (N-Boc-piperazine) or water (e.g., with 1N $Na_2CO_3$) can be added to terminate the reaction. Morpholine also can be added to the reactive polymer solution to terminate the reaction. The crude product was redissolved in methanol and then precipitated from a large excess of diethyl ether. The bottom layer was redissolved in methanol and dried by rotary evaporation and vacuum to give an asymmetrically random branched PEOX polymer as a white solid (101 g). Other POX polymers, initiated by toluenesulfonic acid, such as, linear HPEOX 20, 50, 100, 200, 300 or 500, as well as those initiated by methyl tosylate, such as, linear $CH_3$-PEOX 20, 50, 200, 300 or 500 etc., were prepared in a similar manner. All the products were analyzed by SEC and NMR.

Synthesis of PEOX-Gemcitabine Composition

An EDA-terminated $C_{18}$PEOX100 polymer (see above) (1 gram) was dissolved in 10 mL of methanol. Glycidol (15 mg) was added to the solution and mixed. The solution then was incubated at 40° C. for 2 hours. The resulting polymer was extensively dialyzed against water and then dried using a rotary evaporator. The dry polymer (0.93 g) was dissolved in 6 mL of anhydrous DMF.

The polymer solution (2 mL) was mixed with 97 mg of N,N'-carbonyldiimidazole (CDI) and incubated at 37° C. for 2 hours. The resultant product was precipitated by mixing the reaction mixture with 220 mL of diethyl ether at 4° C. for 16 hours. After removing solvent, gemcitabine (41 mg) was added with 9 mL of water. Sodium carbonate (1 M, 1 mL) was added and the resulting solution was incubated at 4° C.

for 22 hours. The resulting polymer-gemcitabine composition was purified by dialysis against water. Water then was removed with a rotary evaporator. The composite molecule was redissolved in 5 mL of water and then frozen at −70° C.

Testing H460 Lung Cell Survival Rate Following PEOX-Gemcitabine Exposure

H460 cells were suspended at 2000 cells/200 µL in RPMI-1640 medium supplemented with 10% fetal bovine serum, 100 IU/mL penicillin and 100 µg/mL streptomycin. The cells were seeded in the wells of a 96-well microplate. The microplate was incubated for 72 hours at 37° C. with 5% $CO_2$ in air. Thereafter, the culture medium was replaced with 100 µL of fresh cell culture medium containing 0-10,000 ng/ml of gemcitabine or PEOX-gemcitabine composite with an equivalent amount of gemcitabine. All tests were performed in triplicate. Cells were incubated for 72 hours at 37° C. in 5% $CO_2$ in air. CellTiter 96® AQueous One Solution Cell Proliferation Assay (20 µL) from Promega mixed with 100 µL of fresh cell culture medium were added to each well and the plate was incubated for 1 hour at 37° C. The absorbance at 490 nm then was measured using a BioTek EPOCH ELISA plate reader.

Synthesis of PEOX-Camptothecin Composition

Camptothecin (3.48 mg) was added to 1 mL of methylene chloride. CDI (1.62 mg) was added to the mixture which then was stirred at room temperature for 1 hour. EDA-terminated $C_{18}$PEOX100 polymer (see above) (150 mg) was added and incubated at room temperature for 16 hours. The solvent was evaporated to dryness on a rotary evaporator. The resultant solid was redissolved in 3 mL of water, mixed, then filtered through a 0.8 µm syringe filter. The filtrate was frozen at −70° C. for at least 2 hours in a lyophilization vial, then lyophilized overnight (~16 hours). The ready-to-use white powder was stored at −70° C.

Testing MCF-7 Breast Cancer and H460 Lung Cell Survival Rate Following PEOX-Camptothecin Exposure MCF-7 cells were suspended at a density of 6000 cells/200 µL of Eagle's Minimum Essential Medium supplemented with 0.01 mg/mL bovine insulin, 10% fetal bovine serum, 100 IU/mL penicillin and 100 µg/mL streptomycin.

H460 cells were suspended at 2000 cells/200 µL of RPMI-1640 medium supplemented with 10% fetal bovine serum, 100 IU/mL penicillin and 100 µg/mL streptomycin.

The cells were seeded in the wells of a 96-well microplate. The microplate was incubated for 72 hours at 37° C. in 5% $CO_2$ in air. Thereafter, the culture medium was replaced with 100 µL of fresh cell culture medium containing 0-20 µM of camptothecin or PEOX-camptothecin composite, with an equivalent amount of camptothecin. All tests were performed in triplicate. Cells were incubated for 72 hours at 37° C. in 5% $CO_2$ in air. CellTiter 96® AQueous One Solution Cell Proliferation Assay (20 µL) was mixed with 100 µl of fresh cell culture medium and added to each well and the plate was incubated for 1 hour at 37° C. The absorbance at 490 nm then was measured using a BioTek EPOCH ELISA plate reader.

LC-SPDP-PEOX-$NH_2$

To EDA-terminated HPEOX100 polymer, see above, (MW 20000, 20 mg or $1 \times 10^{-6}$ mol) in 200 uL of phosphate buffer (20 mM phosphate and 0.1 M NaCl, pH 7.5) were added $10 \times 10^{-6}$ mol of sulfo-LC-SPDP (Thermo, Rockford, Ill.) in 400 µL of water. The mixture was vortexed and incubated at 30° C. for 30 minutes. The LC-SPDP-PEOX-$NH_2$ was purified by gel filtration chromatography and equilibrated with buffer A (0.1 M phosphate, 0.1 M NaCl and 5 mM EDTA, pH 6.8). The product was concentrated further to yield 500 µL of solution with a concentration of approximately 1.8 nmol/µL.

Preparation of Carboxyl End-Functionalized PEOX

To EDA-terminated H-PEOX100 polymer, see above, (MW 20000, 20 mg or $1 \times 10^{-6}$ mol) in 200 uL of methanol were added $1 \times 10^{-5}$ mol of succinic anhydride (Sigma). The mixture was vortexed and incubated at 40° C. for 120 minutes. The H-PEOX-COOH was purified by dialysis. The water was evaporated to dryness on a rotary evaporator.

Preparation of NHS End-Functionalized PEOX

To the carboxyl end-functionalized H-PEOX100 polymer prepared as taught above (MW 20000, 20 mg or $1 \times 10^{-6}$ mol) in 200 uL of methylene chloride were added $2 \times 10^{-6}$ mol of N,N'-dicyclohexylcarbodiimide (Sigma) and $2 \times 10^{-6}$ mol of N-hydroxysuccinimide (Sigma), and the mixture was incubated at room temperature for 6 hours. After filtration, the reaction mixture was precipitated into diethyl ether at 4° C. for 16 hours. The solvent then was removed.

Preparation of PEOX/C-Reactive Protein Composite

To C-reactive protein (Fitzgerald, Acton, Mass., $2 \times 10^{-7}$ mol) in 5 mL of phosphate buffer (100 mM phosphate and 0.1 M NaCl, pH 7.2) were added $1 \times 10^{-6}$ mol of NHS end-functionalized PEOX polymer prepared as provided above. The reaction was incubated at room temperature for 1 hour. The composite was fractionated on a CM cellulose column (5 ml) with a sodium chloride step gradient in 20 mM phosphate buffer at pH 6. The composite was eluted with a sodium chloride gradient and characterized by ionic exchange chromatography, UV spectroscopy and polyacrylamide gel electrophoresis.

Thiolated PEOX-$NH_2$ from LC-SPDP-PEOX-$NH_2$

The LC-SPDP-HPEOX100-$NH_2$ as described above (50 nmol in 65 ml of buffer A) was mixed with 100 µL of DTT (50 mM in buffer A) and the mixture was allowed to incubate at room temperature for 15 minutes. Excess DTT and byproducts were then removed by gel filtration with buffer A. The product was concentrated in a 10 K Centricon Concentrator to yield 450 µL of thiolated PEOX-$NH_2$ that was used for joining with maleimide-R-activated $_a$ntibody made as described below.

Maleimide R (MAL-R)-Activated Antibody

To antibody in PBS (310 µL, 5.1 mg or 34 nmol) were added 20.4 µL of a MAL-R—NHS (N-hydroxysuccinimide) solution (10 mM in water) (succinimidyl-[(N-maleimidopropionamido)-tetracosaethyleneglycol] ester purchased from ThermoFisher). The mixture was vortexed and incubated at 30° C. for 15 minutes. The product was purified by gel filtration with buffer A. The maleimide-R-activated antibody was used for joining with thiolated compounds, such as, thiolated HPEOX100-$NH_2$.

HPEOX-Antibody Composition

To the thiolated HPEOX100-$NH_2$ prepared as taught above (350 µL or 35 nmol) was added MAL-R-activated antibody (4.8 mL or 34 nmol). The reaction mixture was concentrated to approximately 800 µL and allowed to incubate overnight at 4° C. or at room temperature for about 1 hr. On completion, the reaction was quenched with 100 µL of ethyl maleimide (50 mmolar solution) and the composition then was fractionated on a CM cellulose column (5 ml) with a sodium chloride step gradient in 20 mM phosphate buffer at pH 6. The composition was eluted with a sodium chloride gradient and characterized by ionic exchange chromatography, UV spectroscopy and polyacrylamide gel electrophoresis.

Reduction of Antibody

To antibody, 2.1 mg or 14 nmol in 160 µL of buffer B (containing 0.1 M sodium phosphate, 5 mM EDTA and 0.1 M NaCl, pH 6.0) were added 40 µL of DTT (50 mM in buffer B). The solution was allowed to stand at room temperature for 30 min. The product was purified by gel filtration over a Sephadex G-25 column equilibrated with buffer B. The reduced antibody was concentrated to 220 µL and was used for joining with other molecules.

MAL-R-HPEOX

To EDA-terminated HPEOX in 400 µL (400×10$^{-9}$ mols) at pH 7.4 were added 400 µL of MAL-PEG$_{24}$-NHS (Quanta BioDesign, Powell, Ohio) (10 mM in water). That was mixed and incubated at 30° C. for 15 min. On termination, the product was purified on a Sephadex G-25 column equilibrated with buffer B. The MAL-R-PEOX was collected and stored in aliquots in the same buffer at 40° C.

HPEOX-Antibody Composition

To the reduced antibody described above (14 nmols in 220 µL) was added the MAL-R-HPEOX (154 µL, 16.6 nmols) with stirring. To that were added 12.5 µL of sodium carbonate (1.0 M solution) to bring the pH to ~6.8. The reaction was continued for 1 hr at room temperature. On completion, the reaction was quenched with 100 µL of cysteamine (0.4 mM solution) and the composition then was fractionated on a CM cellulose column (5 ml) with a sodium chloride step gradient in 20 mM phosphate buffer at pH 6. The composition was eluted with a sodium chloride gradient and characterized by ionic exchange chromatography, UV spectroscopy and polyacrylamide gel electrophoresis.

Synthesis of Random Asymmetrically Branched PEOX-PAMAM-1 Copolymer

Random asymmetrically branched C$_{18}$-PEOX-100-NH$_2$ (MW=30,000), methyl acrylate (MA, FW=86.09), ethylenediamine (EDA, FW=60.10), monoethanolamine (MEA, FW=61.08) and methanol were used.

To a round bottom flask were added 10.0 g C$_{18}$-PEOX-100-NH$_2$ and 100 ml methanol (solution A). To a separate round bottom flask were added 86 mg methylacrylate (MA) and 1 ml methanol (solution B). Solution A was then slowly dropped into solution B while stirring at room temperature. The resulting solution was allowed to react at 40° C. for 2 hours. On completion of the reaction, the solvent and unreacted monomer, MA, were removed by rotary evaporation, and the product, MA functionalized C$_{18}$-PEOX-100-NH$_2$, was then redissolved in 100 ml of methanol.

To a round bottom flask were added 5 g EDA and 50 ml of methanol, followed by a slow addition of MA-functionalized C$_{18}$-PEOx-100-NH$_2$ at 0° C. (1 g MA functionalized C$_{18}$-PEOX-100-NH$_2$ dissolved in 10 ml methanol). The solution was then allowed to react at 4° C. for 48 hours. The solvent and the excess EDA were removed by rotary evaporation. The crude product was then precipitated from an ethyl ether solution, and further purified by dialysis to give about 10.076 g random asymmetrically branched PEOX-PAMAM-1.0 copolymer, the theoretical molecular weight is about 30,228. The product was characterized by $^1$H and $^{13}$C nuclear magnetic resonance (NMR) and size exclusion chromatography (SEC).

Other polymers, such as, random asymmetrically branched PEOX-PAMAM-2 (with 2 PAMAM layers and NH$_2$ as surface groups), ran-PEOX-PAMAM-3 (with 3 PAMAM layers and NH$_2$ as surface groups), etc., were prepared by repeating the above synthetic steps, for example, the addition of MA, followed by the reaction with a large excess of EDA. Alternatively, ran-PEOX-PAMAM-2 (OH) (with 2 PAMAM layers and OH as surface groups), and ran-PEOX-PAMAM-3 (OH) (with 3 PAMAM layers and OH as surface groups) and so on can be produced by repeating the above synthetic steps, for example, the addition of MA, followed by reaction with a large excess of MEA.

Additionally, ran-PEOX-PAMAM-2 (NH$_2$/OH) (with 2 PAMAM layers and a mixture of NH$_2$ and OH as surface groups), and ran-PEOX-PAMAM-3 (NH$_2$/OH) (with 3 PAMAM layers and NH$_2$/OH mix as surface groups) can be prepared by repeating the above synthetic steps, for example, the addition of MA, followed by reaction with a mixture of a large excess of EDA/MEA.

All references cited herein are herein incorporated by reference in entirety.

We claim:

1. A functionalized polyoxazoline (POX) polymer composition comprising a first and a second functionalized POX polymer, joined by a difunctional initiator comprising a cleavable disulfide bond, wherein each of said first and said second functionalized POX polymer comprises a water soluble POX polymer reacted with a first linker, L, wherein L is ammonia, or said POX polymer is reacted with an amine group or an imino group of L; L is reacted with a second linker, M; and M is reacted with a bioactive material, B.

2. The polymer composition of claim 1, wherein a B comprises a member of a binding pair (BP), a biologically active molecule (BAM), or a pharmaceutically active agent (PAA).

3. The polymer composition of claim 2, wherein said PAA is selected from the group consisting of a polypeptide or a polynucleotide.

4. The polymer composition of claim 1, wherein said water soluble POX polymers comprises a poly (unsubstituted oxazoline) or a poly(substituted oxazoline).

5. The polymer composition of claim 4, wherein said poly(substituted oxazoline) comprises a poly(2-methyloxazoline), a poly(2-ethyloxazoline), a poly(2-propyloxazoline), a poly(2-butyloxazoline) or a combination thereof.

6. The polymer composition of claim 1, wherein said water soluble POX polymer comprises a linear polymer, a star branched polymer, a combbranched polymer, a dendrimer, a dendrigraft, a hyperbranched polymer, a randomly branched polymer, or a combination thereof.

7. The polymer composition of claim 1, wherein said second linker M comprises a linear polymer, a dendritic polymer, a randomly branched polymer, or a combination thereof.

8. The polymer composition of claim 2, wherein said PAA is selected from the group consisting of paclitaxel, gemcitabine, camptothecin, or a combination thereof.

9. The polymer composition of claim 1, wherein L comprises ethylenediamine, piperazine, 1,4,7,10-tetraazacyclododecane, 4-(aminomethyl)piperidine, 1,3-diaminopropane, 2,2'-(ethylenedioxy)bis(ethylamine), 1,11-diamino-3,6,9-trioxaundecane, diethylenetriamine, hexamethylenediamine, triethylenetetramine, tris(2-aminoethyl)amine, or 1,8-diaminooctane.

10. The polymer composition of claim 1, wherein said second linker M comprises carbodiimide (CDI), a CDI-functionalized molecule, glycidol, succinic anhydride, an acrylic ester, an amidoamine, a linear or a branched polyamidoamine, an acrylamide or a heterofunctional molecule.

11. The polymer composition of claim 10, wherein said heterofunctional molecule comprises an end which is activated with N-hydroxysuccinimide (NHS) or an aldehyde functional group.

12. The polymer composition of claim 1, wherein B is linked to M through a hydrolytically stable or unstable linkage.

13. The polymer composition of claim 1, wherein said initiator comprises 2-(p-toluenesulfonyloxy)ethyl disulfide (TOEDS), (chloromethyl) methyl disulfide, bis(iodomethyl) methyl disulfide, or 2-bromoethyl disulfide.

14. The polymer composition of claim 1, wherein a B comprises a targeting moiety.

15. The polymer composition of claim 14, wherein said targeting moiety comprises an antibody or an antigen-binding portion thereof.

16. The polymer composition of claim 1, wherein B of said first functionalized POX polymer is the same as or is different from B of said second functionalized POX polymer.

17. The polymer composition of claim 1, wherein said initiator comprises

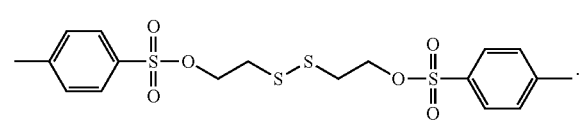

.

* * * * *